United States Patent
Hawkes et al.

(10) Patent No.: US 6,679,883 B2
(45) Date of Patent: Jan. 20, 2004

(54) CERVICAL PLATE FOR STABILIZING THE HUMAN SPINE

(75) Inventors: David T. Hawkes, Draper, UT (US); Thomas M. Sweeney, Sarasota, FL (US)

(73) Assignee: Ortho Development Corporation, Draper, UT (US)

( * ) Notice: Subject to any disclaimer, the term of this patent is extended or adjusted under 35 U.S.C. 154(b) by 0 days.

(21) Appl. No.: 10/198,525

(22) Filed: Jul. 16, 2002

(65) Prior Publication Data

US 2003/0083658 A1 May 1, 2003

Related U.S. Application Data

(60) Provisional application No. 60/335,023, filed on Oct. 31, 2001.

(51) Int. Cl.[7] .............................................. A61B 17/58
(52) U.S. Cl. ......................................... 606/61; 606/73
(58) Field of Search ............................... 606/60, 61, 69, 606/70, 71, 72, 73

(56) References Cited

U.S. PATENT DOCUMENTS

| | | | |
|---|---|---|---|
| 1,385,780 A | * 7/1921 | Dodds | ........................ 411/380 |
| 2,699,774 A | 1/1955 | Livingston | |
| 3,779,240 A | 12/1973 | Kondo | |
| 4,041,939 A | 8/1977 | Hall | |
| 4,388,921 A | 6/1983 | Sutter et al. | |
| RE31,628 E | 7/1984 | Allgower et al. | |
| 4,484,570 A | 11/1984 | Sutter et al. | |
| 4,493,317 A | 1/1985 | Klaue | |
| 4,651,724 A | 3/1987 | Berentey et al. | |
| 4,794,918 A | 1/1989 | Wolter | |
| 4,936,861 A | 6/1990 | Muller et al. | |
| 5,024,213 A | 6/1991 | Asher et al. | |
| 5,041,113 A | 8/1991 | Biedermann et al. | |
| 5,053,036 A | 10/1991 | Perren et al. | |
| 5,057,111 A | 10/1991 | Park | |
| 5,127,912 A | 7/1992 | Ray et al. | |
| 5,127,914 A | 7/1992 | Calderale et al. | |
| 5,147,360 A | 9/1992 | Dubousset | |
| 5,147,361 A | 9/1992 | Ojima et al. | |
| 5,151,103 A | 9/1992 | Tepic et al. | |
| 5,152,303 A | 10/1992 | Allen | |
| 5,180,381 A | 1/1993 | Aust et al. | |
| 5,190,544 A | 3/1993 | Chapman et al. | |

(List continued on next page.)

FOREIGN PATENT DOCUMENTS

| | | |
|---|---|---|
| CA | 1329525 | 9/1994 |
| DE | 3027148 C2 | 5/1982 |
| EP | 0 578 320 A1 | 1/1994 |
| EP | 0 778 007 A1 | 6/1997 |
| FR | 2 732 887 | 10/1996 |
| FR | 2 736 535 | 1/1997 |
| WO | WO 88/03781 | 2/1988 |
| WO | WO 94/16634 | 8/1994 |

*Primary Examiner*—Eduardo C. Robert
*Assistant Examiner*—David Comstock
(74) *Attorney, Agent, or Firm*—Clayton, Howarth & Cannon, P.C.

(57) ABSTRACT

A dynamic spinal fixation plate assembly includes a spinal plate, a receiving member, and a fastener resulting in a low profile orthopedic device. The plate comprises a plurality of holes for maintaining the receiving member. The relationship between the receiving member and the plate allows the plate to adjust during graft settling. The receiving member may be locked to the plate utilizing the mechanical or chemical properties of the device or the receiving member may be configured to rotate freely within the plate hole. Utilizing the features of the present invention, the plate controllably subsides and settles into a position of stability. Additionally, each receiving member has a tapered internal sidewall defining a through hole to matingly engage the fastener, which also has a tapered portion forming a tapered lock-fit between the fastener and the receiving member.

83 Claims, 5 Drawing Sheets

U.S. PATENT DOCUMENTS

| | | |
|---|---|---|
| 5,207,678 A | 5/1993 | Harms et al. |
| 5,209,751 A | 5/1993 | Farris et al. |
| 5,261,911 A | 11/1993 | Carl |
| 5,269,784 A | 12/1993 | Mast |
| 5,290,288 A | 3/1994 | Vignaud et al. |
| 5,300,073 A | 4/1994 | Ray et al. |
| 5,324,290 A | 6/1994 | Zdeblick et al. |
| 5,364,399 A | 11/1994 | Lowery et al. |
| 5,376,125 A | 12/1994 | Winkler |
| 5,395,371 A | 3/1995 | Miller et al. |
| 5,403,314 A | 4/1995 | Currier |
| 5,423,826 A | 6/1995 | Coates et al. |
| 5,429,639 A | 7/1995 | Judet |
| 5,443,467 A | 8/1995 | Biedermann et al. |
| 5,474,555 A | 12/1995 | Puno et al. |
| 5,480,401 A | 1/1996 | Navas |
| 5,486,176 A | 1/1996 | Hildebrand et al. |
| 5,498,263 A | 3/1996 | DiNello et al. |
| 5,501,684 A | 3/1996 | Schlapfer et al. |
| 5,514,184 A | 5/1996 | Doi et al. |
| 5,520,690 A | 5/1996 | Errico et al. |
| 5,531,746 A | 7/1996 | Errico et al. |
| 5,534,027 A | 7/1996 | Hodorek |
| 5,549,608 A | 8/1996 | Errico et al. |
| 5,549,612 A | 8/1996 | Yapp et al. |
| 5,554,157 A | 9/1996 | Errico et al. |
| 5,558,674 A | 9/1996 | Heggeness et al. |
| 5,578,034 A | 11/1996 | Estes |
| 5,586,984 A | 12/1996 | Errico et al. |
| 5,591,166 A | 1/1997 | Bernhardt et al. |
| 5,601,553 A | 2/1997 | Trebing et al. |
| 5,607,426 A | 3/1997 | Ralph et al. |
| 5,616,144 A | 4/1997 | Yapp et al. |
| 5,643,265 A | 7/1997 | Errico et al. |
| 5,647,873 A | 7/1997 | Errico et al. |
| 5,669,911 A | 9/1997 | Errico et al. |
| 5,672,176 A | 9/1997 | Biedermann et al. |
| 5,676,666 A | 10/1997 | Oxland et al. |
| 5,676,703 A | 10/1997 | Gelbard |
| 5,681,311 A | 10/1997 | Foley et al. |
| 5,681,319 A | 10/1997 | Biedermann et al. |
| 5,690,630 A | 11/1997 | Errico et al. |
| 5,713,900 A | 2/1998 | Benzel et al. |
| 5,725,588 A | 3/1998 | Errico et al. |
| 5,733,285 A | 3/1998 | Errico et al. |
| 5,733,286 A | 3/1998 | Errico et al. |
| 5,735,850 A | 4/1998 | Baumgartner et al. |
| 5,735,853 A | 4/1998 | Olerud |
| 5,766,254 A | 6/1998 | Gelbard |
| 5,797,912 A | 8/1998 | Runciman et al. |
| 5,800,435 A | 9/1998 | Errico et al. |
| 5,807,396 A | 9/1998 | Raveh |
| 5,817,094 A | 10/1998 | Errico et al. |
| D402,032 S | 12/1998 | Stone |
| D406,646 S | 3/1999 | Stone |
| 5,876,402 A | 3/1999 | Errico et al. |
| 5,882,350 A | 3/1999 | Ralph et al. |
| 5,888,204 A | 3/1999 | Ralph et al. |
| 5,902,303 A | 5/1999 | Eckhof et al. |
| 5,904,683 A | 5/1999 | Pohndorf et al. |
| 5,910,142 A | 6/1999 | Tatar |
| 5,954,722 A | 9/1999 | Bono |
| 5,968,046 A | 10/1999 | Castleman |
| 6,017,345 A | 1/2000 | Richelsoph |
| 6,022,350 A | 2/2000 | Ganem |
| 6,030,389 A | 2/2000 | Wagner et al. |
| 6,036,693 A | 3/2000 | Yuan et al. |
| 6,080,193 A | 6/2000 | Hochshuler et al. |
| 6,102,951 A | 8/2000 | Sutter et al. |
| 6,117,173 A | 9/2000 | Taddia et al. |
| 6,129,730 A | 10/2000 | Bono et al. |
| 6,139,550 A | 10/2000 | Michelson |
| 6,152,927 A | 11/2000 | Farris et al. |
| 6,159,213 A | 12/2000 | Rogozinski |
| 6,187,005 B1 | 2/2001 | Brace et al. |
| 6,193,720 B1 | 2/2001 | Yuan et al. |
| 6,193,721 B1 | 2/2001 | Michelson |
| 6,206,881 B1 | 3/2001 | Frigg et al. |
| D440,311 S | 4/2001 | Michelson |
| 6,214,005 B1 | 4/2001 | Benzel et al. |
| 6,224,602 B1 | 5/2001 | Hayes |
| 6,228,085 B1 | 5/2001 | Theken et al. |
| 6,231,610 B1 | 5/2001 | Geisler |
| 6,235,033 B1 | 5/2001 | Brace et al. |
| 6,235,034 B1 | 5/2001 | Bray |
| 6,241,731 B1 | 6/2001 | Fiz |
| 6,258,089 B1 | 7/2001 | Campbell et al. |
| 6,261,291 B1 | 7/2001 | Talaber et al. |
| 6,273,889 B1 | 8/2001 | Richelsoph |
| 6,290,703 B1 | 9/2001 | Ganem |
| 6,331,179 B1 | 12/2001 | Freid et al. |
| 6,428,542 B1 | 8/2002 | Michelson |
| 2001/0014807 A1 | 8/2001 | Wagner et al. |
| 2001/0021851 A1 * | 9/2001 | Eberlein et al. ............... 606/69 |
| 2003/0040749 A1 * | 2/2003 | Grabowski et al. ........... 606/71 |

* cited by examiner

CERVICAL PLATE FOR STABILIZING THE HUMAN SPINE

CROSS-REFERENCE TO RELATED APPLICATIONS

This application claims the benefit of U.S. Provisional Application No. 60/335,023, filed Oct. 31, 2001, which is hereby incorporated by reference herein in its entirety, including but not limited to those portions that specifically appear hereinafter.

STATEMENT REGARDING FEDERALLY SPONSORED RESEARCH OR DEVELOPMENT

Not Applicable.

BACKGROUND OF THE INVENTION

1. The Field of the Invention

The present invention relates generally to orthopedic bone fixation devices for stabilizing a plurality of bone segments, and more particularly, but not necessarily entirely, to a bone plate and a bone screw assembly for stabilizing the cervical spine and blocking movement of grafts, and otherwise maintaining the cervical vertebrae in a desired relationship.

2. Description of Related Art

The spine is a flexible, multi-segmented column that supports the upright posture in a human while providing mobility to the axial skeleton. The spine serves the functions of encasing and protecting vital neural elements and provides structural support for the body by transmitting the weight of the body through the pelvis to the lower extremities. Because there are no ribs attached to either the cervical spine or the lumbar spine, they have a relatively wide range of motion.

The spine is made up of bone, intervertebral discs, synovial joints with their articular cartilage, synovial capsules and, as part of the back, is surrounded by supporting ligaments, muscle, fascia, blood vessels, nerves, and skin. As in other areas of the body, these elements are subject to a variety of pathological disturbances: inflammation, trauma, neoplasm, congenital anomalies, disease, etc. In fulfilling its role in the back, the spine can be subjected to significant trauma which plays a dominant role in the etiology of neck and low back pain. Trauma frequently results in damage at the upper end of the lumbar spine, where the mobile lumbar segments join the less mobile dorsal spine. Excessive forces on the spine not only produce life-threatening traumatic injuries, but may contribute to an increased rate of degenerative change.

The cervical spine comprises the first seven vertebrae of the spine, which begin at the base of the skull and end at the upper torso. Because the neck has a wide range of motion and is the main support for the head, the neck is extremely vulnerable to injury and degeneration.

Spinal fixation has become a common approach in treating spinal disorders, fractures, and for fusion of the vertebrae. One common device used for spinal fixation is the bone fixation plate. Generally, there are two types of spinal plates available, (i) constrained plates and (ii) semiconstrained plates. Generally, a constrained plate completely immobilizes the vertebrae and does not allow for graft settling. In contrast, a semiconstrained plate is dynamic and allows for a limited degree of graft settling through micro-adjustments made between the plate and bone screws attaching the plate to the spine perhaps by way of an intervening coupling ring that holds the screws within the plate. The operation of the semiconstrained plate stimulates bone growth. Each type of plate has its own advantages depending upon the anatomy and age of the patient, and the results desired by the surgeon.

A typical bone fixation plate includes a relatively flat, rectangular plate having a plurality of holes formed therein. A corresponding plurality of bone screws may be provided to secure the bone fixation plate to the vertebrae of the spine.

A common problem associated with the use of bone fixation plates is the tendency for bone screws to become dislodged and "back out" from the bone, thereby causing the plate to loosen. Some attempts to provide a screw with polyaxial capabilities to help avoid screw "back out" are known throughout the prior art. However, many of these attempts have resulted in a bone fixation plate having a very large profile size that can cause irritation and discomfort in the patient's spinal region, or an assembly with multiple parts that must be assembled prior to implantation, which can be laborious and time consuming for surgeons.

In a typical anterior cervical fusion surgery, the carotid sheath and sternocleidomastoid muscles are moved laterally and the trachea and esophagus are moved medially in order to expose the cervical spine. The cervical plate is designed to lie near and posterior to the esophagus. Due to its relative location to the esophagus and other connective tissue, if the bone screw securing the plate to the cervical spine backs out, the bone screw could pierce the esophagus, causing not only pain and infection, but also posing a serious risk of death to the patient. The anti-back out mechanism is important not only to avoid piercing of the esophagus, but also to reduce the profile size of the plate, such that no post-operative difficulty in swallowing is experienced by the patient.

There are several spinal fixation devices known in the prior art. U.S. Pat. No. 6,193,720 (granted Feb. 27, 2001 to Yuan et al.) discloses a cervical spine stabilization device. This cervical spine fixation device requires multiple component parts to provide fixation between a plurality of vertebrae. This device is complex in operation because it requires multiple parts, each of which must be adjusted by the surgeon during surgery, causing extra unnecessary and unwanted labor and time.

U.S. Pat. No. 6,022,350 (granted Feb. 8, 2000 to Ganem) discloses a bone fixation device comprising an elongate link for receiving at least one bone-fastening screw containing a semi-spherical head, which bone-fastening screw passes through an orifice created in the elongate link. The bottom of the elongate link contains a bearing surface that essentially has a circular cross section, allowing the semispherical head to be seated therein. The device further includes a plug having a thread suitable for coming into clamping contact against the screw head to hold the head in a desired angular position. This device is characterized by several disadvantages, including the need for a larger profile fixation device in order to allow the semi-spherical bone-fastening screw head and the accompanying plug to fit within the bearing surface. Ganem's larger profile design reduces the effectiveness of the device because of the potential for increased discomfort for the patient.

It is noteworthy that none of the prior art known to applicants provides a spinal fixation device having a low profile size, utilizes few component parts, and provides the surgeon with the ability to manipulate and micro-adjust the fixation device. There is a long felt, but unmet, need for a spinal fixation device which is relatively inexpensive to make, simple in operation and provides a secure interlock between the head of a fastener, such as a bone screw, and the inner sidewall of a receiving member, which is located within a plate hole, that also has a low profile.

The prior art is thus characterized by several disadvantages that are addressed by the present invention. The present invention minimizes, and in some aspects eliminates, the above-mentioned failures, and other problems, by utilizing the methods and structural features described herein.

The features and advantages of the invention will be set forth in the description which follows, and in part will be apparent from the description, or may be learned by the practice of the invention without undue experimentation. The features and advantages of the invention may be realized and obtained by means of the instruments and combinations particularly pointed out in the drawings, subsequent detailed description and appended claims.

BRIEF DESCRIPTION OF THE DRAWINGS

The above and other features and advantages of the invention will become apparent from a consideration of the subsequent detailed description presented in connection with the accompanying drawings in which.

DETAILED DESCRIPTION OF THE INVENTION

Figure 1:
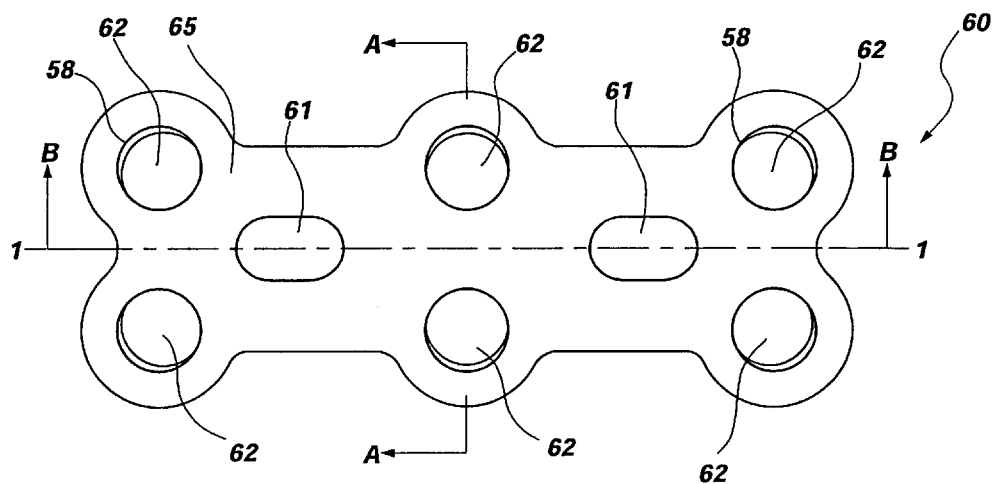
FIG. 1 is a top view of a dynamic spinal plate illustrated with three pairs of holes for implantation purposes, made in accordance with the principles of the present invention.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Before the present device and methods for implantation of said device are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

Figure 2:
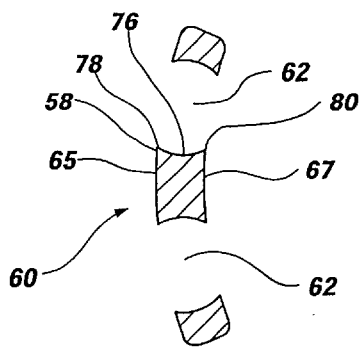
FIG. 2 is a cross-sectional view of the dynamic spinal plate taken along section A—A of FIG. 1.
Figure 3:
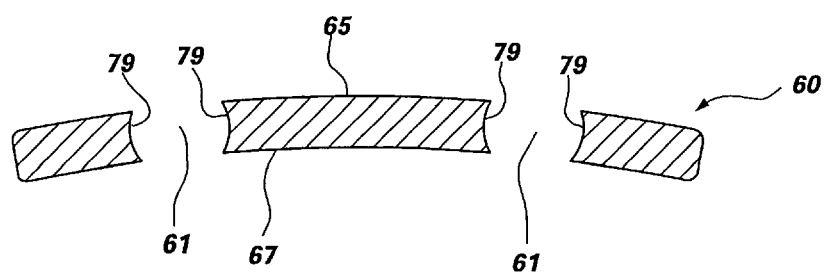
FIG. 3 is a side, cross-sectional view of the dynamic spinal plate taken along section B—B of FIG. 1.

Referring now to the drawings, FIGS. 1–3 illustrate an elongate member in the form of a spinal plate made in accordance with the principles of the present invention, and more particularly a cervical plate designated generally at 60. The elongate member 60, also referred to herein as an attachment member, and its component parts may be manufactured from any suitable biocompatible material, including metal, such as titanium, stainless steel, cobalt-chromium-molybdenum alloy, titanium-aluminum vanadium alloy or other suitable metallic alloys, or non-metallic biocompatible materials such as carbon-fiber, ceramic, bio-resorbable materials or if desired any suitable high strength plastic such as an ultra high molecular weight polyethylene. It will be appreciated by those skilled in the art that other biocompatible materials, whether now known or later discovered, may be utilized by the present invention, and said biocompatible materials are intended to fall within the scope of the present invention.

Figure 7:
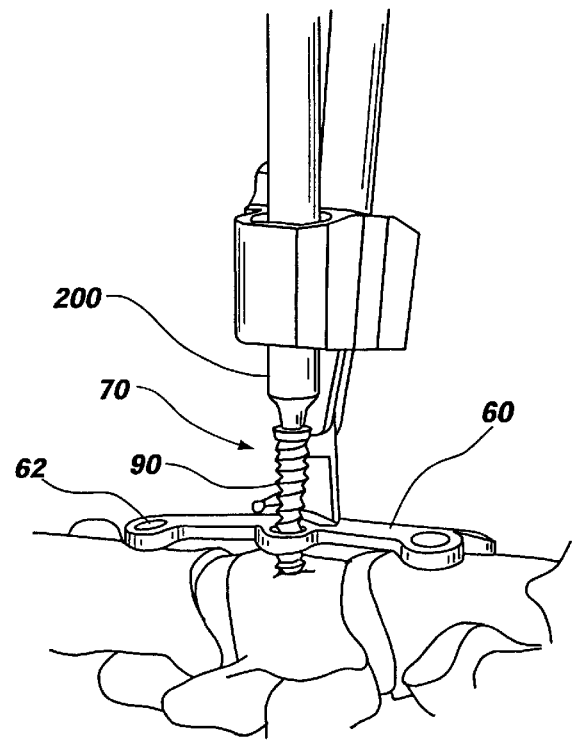
FIG. 7 is a side view of a spinal plate system and a driving instrument inserting a bone screw through a cervical plate and into the cervical spine, made in accordance with the principles of the present invention.
Figure 8:
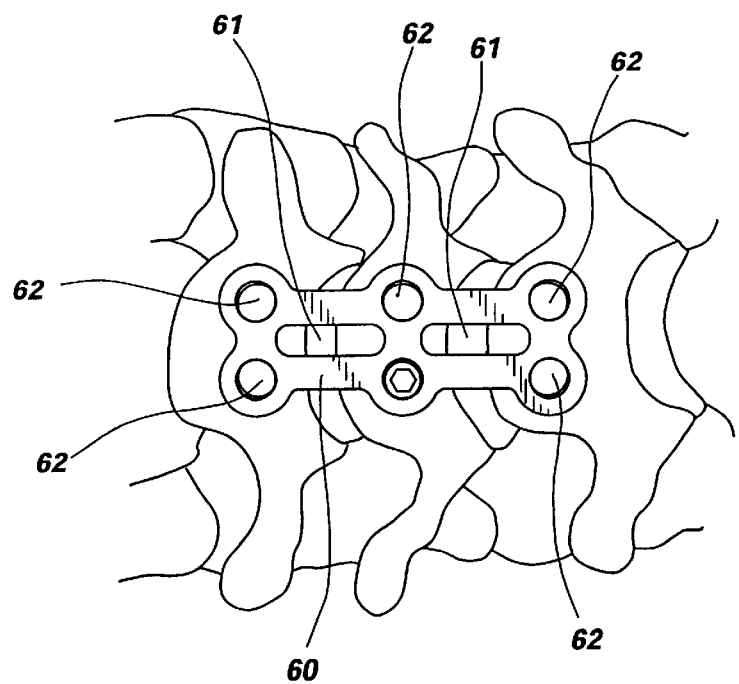
FIG. 8 is a top view of the spinal plate system of FIG. 7, having a single bone screw inserted through a collet or receiving member (not visible), through the plate and into the cervical spine in accordance with the principles of the present invention.

The plate 60 may be configured and dimensioned for being installed on the spine, and more particularly on the anterior portion of the cervical spine as illustrated in FIGS. 7 and 8. While the features and principles of the present invention are largely illustrated and described herein as a spinal plate 60, it will be appreciated that the spinal plate 60 is merely one example of how the present invention may be used and the principles of the present invention may be applied to other orthopedic devices, which will be described herein in more detail.

Referring back to FIGS. 1–3, the plate 60 is illustrated as having a top surface 65 and a bottom surface 67, with plate holes 62 formed in the plate 60 and extending between said top 65 and bottom 67 surfaces. A circumferential edge 58 of the plate holes 62 defines the diameter of said plate holes 62, while encircling the openings of the plate holes 62, and further defines an exterior boundary of a retaining lip 78, which may be disposed beneath the circumferential edge 58. Plate holes 62 may be circularly shaped and may be configured and dimensioned to accept a receiving member 64 such that the receiving member 64 may be retained by said retaining lip 78 within said plate hole 62.

While the shape of the plate holes 62 are illustrated herein as being circular, it should be noted that other shapes could also be used for the plate holes 62, such as elongated holes, or any other suitably shaped plate holes 62 that perform functions similar to the circular plate holes 62 described herein. Accordingly, any suitable shape for holes 62 is useable, whether round, oblong, or even asymmetrical in shape, and each of the above plate holes 62 is intended to fall within the scope of the present invention.

The plate 60 illustrated in FIG. 1 has three pairs of plate holes 62, with each hole of a pair of plate holes 62 residing on either side of longitudinal axis 1—1, and may be used as a 2-level fusion plate. That is, the plate 60 may be sized to span two levels of vertebrae with two discs sandwiched between three successive vertebrae (seen best in FIGS. 7 and 8). As illustrated in FIG. 1, each hole within a pair of plate holes 62 may be spaced apart from its mate such that the plate holes 62 of each pair reside equidistantly on each side of the longitudinal axis 1—1 of FIG. 1. Alternatively, the three pairs of plate holes 62 may be located within the plate 60 such that no particular spacial relationship exists between them. It should be noted that the plate holes 62 may be located within the plate 60 in any suitable arrangement such that the plate holes 62 are located over a section of vertebral bone for implanting a fastener 70 into the vertebral bone to secure the plate or elongate member 60 to the vertebral bone.

It should be further noted that a 3-level fusion plate (not illustrated in the figures) may be sized to span three intervertebral discs, and may have eight plate holes 62 or four pairs of plate holes for connecting the plate to four vertebrae of the spine. It should be noted that the number of holes 62 in the fusion plate may comprise less than a pair of holes per vertebrae spanned and to which the plate is connected. In other words, in the present invention there is no requirement that the plate contain a pair of holes at each level of vertebral fusion. For example, a 3-level fusion plate may contain eight holes, or four pair of holes, as described above, or the plate may contain less than eight holes, and still accomplish a 3-level fusion. For example, the plate may be designed to span four vertebrae, but only include six screw holes or four screw holes located either symmetrically or asymmetrically within the plate. The same concept holds true for each and every plate sized to span any number of vertebrae of the spine.

It is to be understood that any size or level of intervertebral fusion may be accomplished by the invention, by modifying the plate 60 to be of any size to fuse the desired number of vertebrae. For example, to fuse a greater number of vertebrae additional plate holes 62 may be added and the plate 60 elongated. Conversely, to fuse less vertebrae the plate holes 62 may be reduced in number and the plate 60 may be decreased in size. It should be noted that in the modification of the plate 60, it is the size of the plate 60 that defines how many vertebrae may be fused, and one of skill in the art could readily identify the appropriate number of plate holes 62 required for securing said plate 60 to the spine.

Figure 4:
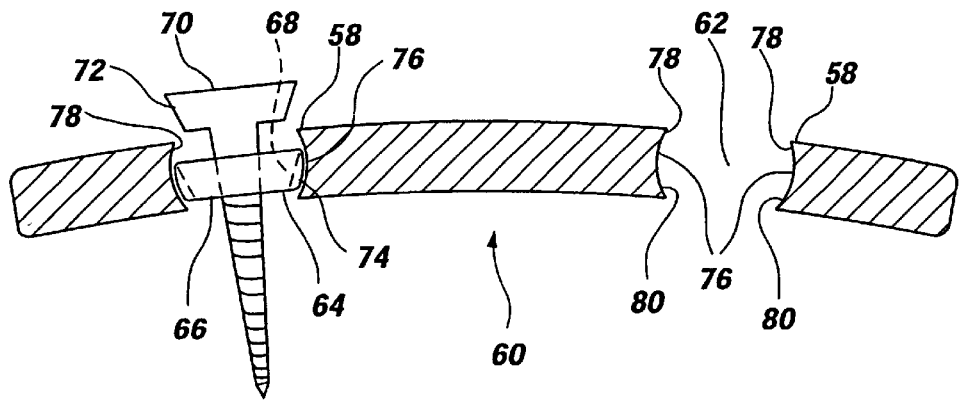
FIG. 4 is a schematic, side view of the dynamic spinal plate taken along section A—A of FIG. 1, illustrated in connection with a receiving member and a bone screw disposed within said spinal plate.

As illustrated in FIGS. 2 and 4, the retaining lip 78, sometimes referred to herein as a retaining member or a means for retaining a receiving member 64, extends laterally from plate holes 62 and may be formed near or as an extension of the top surface 65 of the plate 60 and may be associated with the circumferential edge 58. Because the receiving member 64 may be designed and sized to move within the plate holes 62, the retaining lip 78 functions to maintain said receiving member 64 within the plate hole 62 by acting as a retaining barrier such that the receiving member 64 may contactably engage the retaining lip 78 to thereby prevent the receiving member 64 from exiting the plate hole 62. It will be appreciated that the retaining lip 78 may extend completely around the entire opening of the plate hole 62 or the retaining lip 78 may be modified such that the retaining lip 78 only extends partially around the opening of the plate hole 62.

Referring again to FIG. 1, through holes 61 may be located in the center portion along the longitudinal axis 1—1 of the plate 60 for the surgeon's convenience in adjusting the plate 60 to the desired position on the spine. The through holes 61 may be elongated to allow settling or subsidence of the bone graft. The through holes 61 may have a retaining lip 79, as illustrated in FIG. 3, which may be similar to retaining lip 78 surrounding at least a portion of the plate hole 62, or there may be no retaining lip 79 present at all (a condition not shown in the figures). In the latter case, there would be only a circumferential edge similar to the circumferential edge 58 surrounding plate holes 62.

Figure 5:
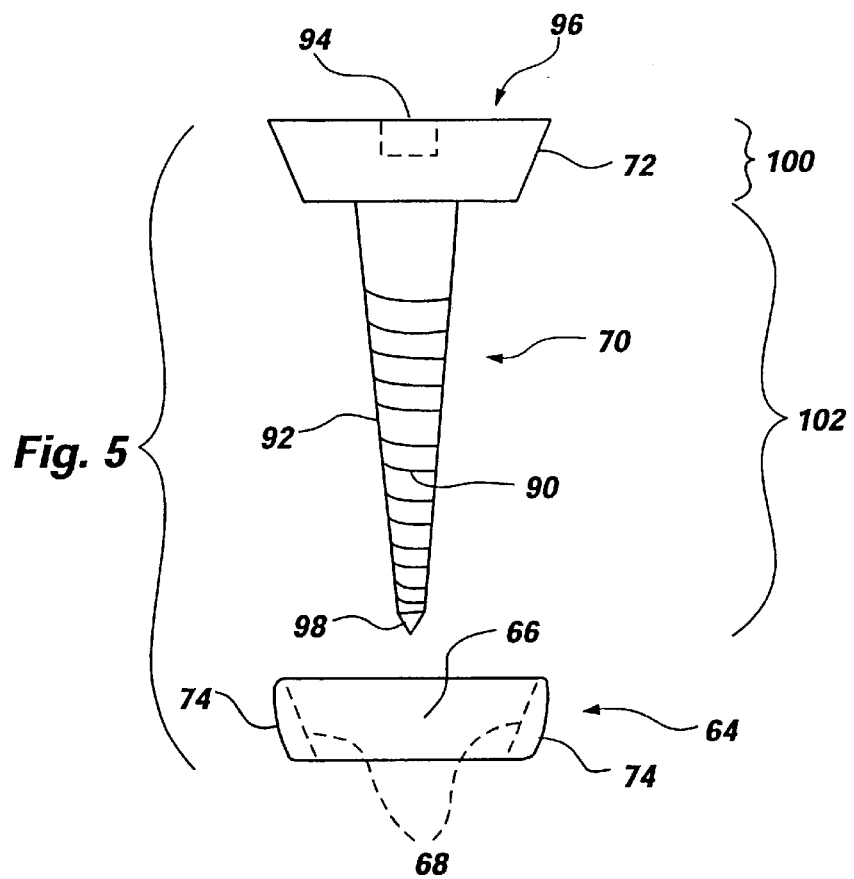
FIG. 5 is an enlarged, exploded side view of the bone screw and receiving member illustrated in FIG. 4.

Referring now to FIG. 5, an enlarged, exploded view of one embodiment of a fastener 70 with a receiving member 64 is illustrated, wherein the fastener 70 comprises a first portion 100 and a second portion 102. The first portion 100 may comprise a head 96 having a tapered section 72, wherein the head 96 may include a recess 94 formed therein for receiving an instrument 200 (seen best in FIG. 7), which instrument 200 may be configured for driving the fastener 70 into the vertebral bone. It should be noted that the tapered section 72 may be formed on the full length of the head 96 as illustrated in FIG. 5 or the tapered section 72 may be formed on a portion of the head 96. It will be appreciated that the tapered section 72 of the first portion 100 may be located on any suitable section of the fastener 70, including the head 96, such that the tapered section 72 may mate with tapering sidewalls 68 defining a tapered section of the receiving member 64 and any such modification is contemplated by and intended to fall within the scope of the present invention.

The second portion 102 may comprise a shaft 92 containing threads 90, and a tip 98. As used herein, fastener 70 may sometimes be referred to as a screw, bone screw, or as a means for attaching the elongate member 60 to at least one human vertebra. It should be noted, however, that the fastener 70 may be a bone screw, bolt, threadless pin, or any other suitable fastener for attaching the elongate member 60 to at least one human vertebra.

It will be appreciated that the structure and apparatus disclosed herein is merely one example of a means for attaching the elongate member 60 to at least one human vertebra of the spine, and it should be appreciated that any structure, apparatus or system for attaching the elongate member 60 to at least one human vertebra of the spine, which performs functions the same as, or equivalent to, those disclosed herein are intended to fall within the scope of a means for attaching, including those structures, apparatus or systems for attaching an elongate member 60 to at least one human vertebra of the spine which are presently known, or which may become available in the future. Anything which functions the same as, or equivalently to, a means for attaching an elongate member 60 to the spine falls within the scope of this element.

Figure 6:
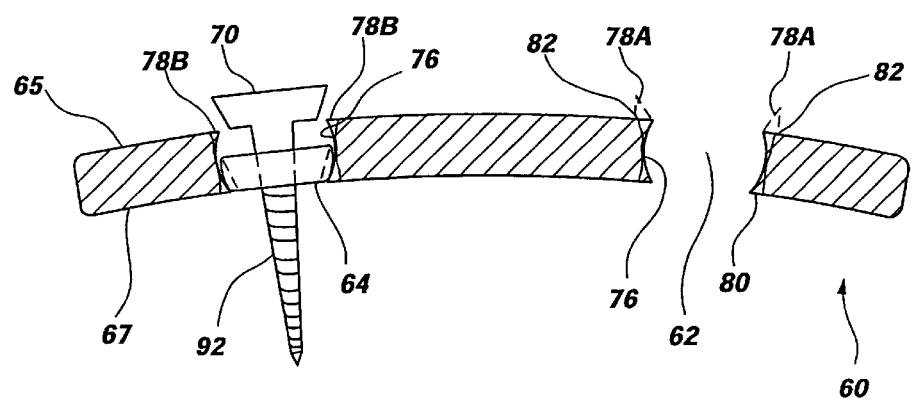
FIG. 6 is a schematic, side view of the dynamic spinal plate taken along section A—A of FIG. 1, illustrating another embodiment of a retaining lip.

Referring now to FIGS. 4, 5, and 6, the plate 60 may be designed to achieve a "constrained" or "semiconstrained" level of stabilizing support determined, in part, by the relationship between each plate hole 62 and a corresponding receiving member 64, sometimes referred to herein as a means for receiving a fastener 70. While the receiving member 64 is illustrated herein as being a circular ring, it should be noted that other shapes could also be used for the receiving member 64 such as oblong, square, polygonal or any other suitable shape, and any receiving member that performs functions the same as or similar to the receiving member 64 described herein is intended to fall within the scope of the present invention. Accordingly, any suitable shape for the receiving member is useable, including but not limited to round, oblong, square, polygonal or even asymmetrical shapes.

The receiving member 64 includes a through-passage 66, which may be defined by tapering walls such as frustoconical, tapered sidewalls 68. The sidewalls 68 may further be characterized as Morse-tapered sidewalls. The tapered section 72 of the fastener 70 may be designed to lockably mate with the tapered sidewalls 68 of the through passage 66 of the receiving member 64 in a friction fit. The mating engagement between the tapered section 72 and the sidewalls 68 may be characterized as self-locking. It should be noted that the taper angle of the sidewalls 68 of the receiving member 64 and the taper angle of tapered section 72 of the fastener 70 may be any suitable taper angle such that a self-locking taper may be formed. It will be appreciated that the receiving member 64 may be configured such that it is not caused to expand responsive to the fastener 70. In other words, the tapered section 72 of the fastener 70 in this embodiment is not intended to cause expansion of said receiving member 64 into engagement against the sidewall 68 of the receiving member 64, but rather the receiving member 64 does not expand responsive to application of the fastener 70. However, it should be noted that the receiving member 64 may, if desired, be configured with a slit, gap, or other mechanism for expanding and contracting said receiving member 64.

The plate 60 of the present invention may be classified as a "restricted backout" plate, wherein the receiving member 64 essentially locks the fastener 70 to the plate 60 such that fastener backout is restricted. This function, and the structure to support it, are explained below in more detail.

Restricted backout systems such as the present invention, may be classified into two subcategories: (i) constrained plates and (ii) semiconstrained plates. In a restricted backout plate, the fastener 70 may either be fully constrained and locked with respect to the plate 60 such that substantially no movement may be allowed in the fastener-plate interface, or alternatively the fastener 70 may be allowed to rotate or translationally move in relation to the plate 60 in a semi-constrained manner that enables a plurality of angular orientations in which the fastener 70 may be implanted into the spine. A plate 60 that restricts backout and is semiconstrained may allow each fastener 70 and receiving member 64 combination to rotate within the plate hole 62 about the longitudinal axis of the fastener 70, or may allow each fastener 70 and receiving member 64 combination to slide within the plate hole 62 in a back-and-forth translational manner, or the plate 60 may allow a combination of the two, allowing some fastener 70 and receiving member 64 combinations to rotate and others to slide translationally. By operation of these structural and functional characteristics, semiconstrained systems permit controlled subsidence of the plate 60. The present invention includes a novel, unique design having aspects of a semiconstrained plating system that allows for both rotational motion and translational motion.

As part of the novel, unique design of the current invention, the receiving member 64 includes an arcuate or curvate exterior surface 74, which may also be described as a convex exterior surface 74, that fits within the plate holes 62, and complements an arcuate or curvate interior surface 76 of said plate holes 62, which may also be described as a concave interior surface 76 of the plate holes 62. The receiving member 64 may be designed such that the convex exterior surface 74 can be either fully engaged or partially engaged with the corresponding concave interior surface 76 of the plate hole 62, in either case, the fastener 70 may be essentially locked to the plate 60. The receiving member 64 of the present invention includes multiple embodiments. In a first "constrained plate" embodiment, the receiving member 64 locks to the plate 60 as the fastener 70 is tightened and secured to the receiving member 64. The structure to accomplish this locking feature subsists in the receiving member 64 comprising a rough surface finish on the exterior surface 74 such that when the fastener 70 is inserted and tightened to the receiving member 64, said receiving member 64 locks to the plate 60 by way of the rough surface finish. As used herein, the phrase "rough surface finish" may be defined as a surface having textural inequalities, or ridges, or projections, while the term "smooth" may be defined as having a continuous even surface without any textural inequalities, or ridges, or projections detectable by an average human observer. The rough surface described above may be mechanical or chemical and may be used to create the locking mechanism between the receiving member 64 and the plate 60.

The mechanical lock occurs by way of the receiving member 64 having a rough surface finish to thereby engage in an enhanced frictional engagement with the corresponding interior surface 76 of the plate hole 62. The interior surface 76 may have a smooth surface finish, or alternatively the interior surface may have a rough surface finish. Thus, the surface roughness of one or both of those components provides the mechanical qualities sufficient to cause the receiving member 64 to essentially lock to the plate 60 by way of a friction fit.

Another manner in which the receiving member 64 may be essentially locked to the plate in a constrained manner is through chemical properties that can be present in, or added to, the surface of one or both of items 64 and 76, as known and understood by those of ordinary skill in the art. For example, a common material used to manufacture orthopedic devices is titanium or any of its alloys. When two pieces of titanium are placed in close proximity together, chemical properties can be used to lock the two pieces together.

In another illustrative "constrained plate" embodiment for essentially locking the receiving member 64 to the plate 60, the receiving member 64 must be large enough to remain in contact with the interior surface 76 of the plate hole 62. Such a contact may be accomplished using a difference in the radii of curvature of said receiving member 64 and said interior surface 76 of the plate hole 62, such that the difference in radii of curvature between those two components creates a lock. Specifically, the lock occurs at a zone of contact corresponding to the difference in the radii of curvature between the exterior surface 74 of the receiving member 64 and the interior surface 76 of the plate hole 62. The zone of contact may include a discrete circumferential contact line, or a wider circumferential band of contact that would be wide enough not to be considered a line of contact. Thus, the receiving member 64 is maintained within the plate hole 62 because of the difference in the radii of curvature between components.

In an alternative "semiconstrained plate" embodiment, the convex exterior surface 74 of the receiving member 64 may be partially engaged with the corresponding concave interior surface 76 of the plate holes 62, or even removed from such engagement by a smaller design of member 64. The receiving member 64 may be designed to be small enough to remain movable within the plate hole 62 during partial engagement such that (i) if the receiving member 64 is in contact with the concave interior surface 76, such contact is a semiconstrained, movable, dynamic frictional contact; or (ii) only a portion of the convex exterior surface 74 of the receiving member 64 resides in contact with the concave interior surface 76 of the plate hole 62; or (iii) the receiving member 64 may be designed to not even touch the concave interior surface 76 at all and may be retained only by the retaining lip 78. In any of these alternative structural embodiments, the receiving member 64 may be rotated and moved translationally within the plate hole 62 in a "semiconstrained" manner even after the tapered section 72 of the fastener 70 is inserted into and engages the tapered sidewall 68 of the receiving member 64. This partially engaged "semiconstrained" relationship between the receiving member 64 and the interior surface 76 of the plate hole 62 permits micro-adjustments of the plate 60 on the spine.

As described above in relation to the "semiconstrained plate" system, the receiving member 64 may be designed to be rotated within the plate hole 62 such that the receiving member 64 may move freely. Such "semiconstrained" embodiments may be accomplished with or without a match of radii of curvature between the exterior surface 74 of the receiving member 64 and the interior surface 76 of the plate hole 62, by designing the size of the plate hole 62 to be large enough to permit "semiconstrained" movements, or the receiving member 64 may be designed to be small enough to permit the member 64 to move in a rotational and translational manner. In such embodiments, the exterior surface 74 of the receiving member 64 and the interior surface 76 of the plate hole 62 may both be smooth. Additionally, the radii of curvature of the receiving member 64 and the interior surface 76 of the plate hole 62 may be configured to match each other, without regard to whether or not the receiving member 64 is engaged with the interior surface 76. The above configurations permit rotation and also slight translational movement of the receiving member 64.

The ability of the receiving member 64 to move within the plate holes 62, permits the entire plate 60 to controllably subside or settle. The slight movement allowed between the plate 60 and the receiving member 64 defines a "semiconstrained" state of the plate 60. In order for the receiving member 64 to be partially engaged with the plate 60, the receiving member 64 may be smaller than the corresponding interior of the plate hole 62 in order to allow the requisite movement. However, the receiving member 64 should not be so small as to permit the receiving member 64 to slide past the retaining lip 78 or a lower rim 80 and separate itself from the plate 60.

Likewise, the receiving member 64 and the plate 60 may have a geometry such that the receiving member 64 may be movable, but cannot flip over itself or flip 180 degrees from its original position, with respect to a horizontal axis, while it is maintained within the plate hole 62. Thus, the retaining lip 78 is able to maintain each embodiment of the receiving member 64 without changing the shape or design of the retaining lip 78.

Further, the present invention allows the receiving member 64 to lock in one-step with the fastener 70 permitting the surgeon to quickly and efficiently insert the fastener 70 into the spine without undue delay. Because the receiving member 64 may be pre-installed within plate holes 62 of the plate 60 during the manufacturing process or prior to surgery, the surgeon simply has to implant the fastener 70 in the desired location to attach the entire assembly 60 to the spine. This may be accomplished by inserting the shaft 92 of the fastener 70 through the through-passage 66 of the receiving member 64 engaging the tapered interlock fit between the tapered section 72 of the fastener 70 and the tapered sidewall 68 of the receiving member 64 described above.

Once the fastener 70 has been locked within the receiving member 64, which receiving member 64 may be located within each hole 62 of the plate 60, and secured to an appropriate bone of the spine, the plate 60 is positioned in a semiconstrained state. Thus, some movement between the receiving member 64 and the plate 60 is permitted by the movable position of the arcuate-exterior surface 74 of the receiving member 64 within the concave-interior 76 of the plate hole 62. As such, the plate 60 may be implanted and may be allowed to settle into a position of stability. The slight movements permitted between the receiving member 64 and the plate 60 permit micro-adjusting, which reduces the mechanical stress transfers between the plate 60 and the human spine to which it is attached.

The receiving member 64 may be configured and dimensioned such that the diameter of the receiving member 64, at its widest point, may be large enough in size to inhibit the receiving member 64 from exiting the confines of the plate hole 62.

Installation of the receiving member 64 within the plate 60 may be accomplished at room temperature due, at least in part, to the elasticity of the material used to manufacture both the receiving member 64 and the plate 60. Room temperature installation may be achieved by elastic deformation of the receiving member 64 and the plate 60. The term "elastic deformation" may be defined herein as the deformation of a body in which the applied stress is small enough so that the object retains its original dimensions once the stress is released.

It is important to note that the receiving member 64 and the plate 60 elastically deform and do not undergo substantial plastic deformation. The term "plastic deformation" may be defined herein as the substantial deformation of a body caused by an applied stress which remains after the stress is removed. It will be appreciated that the stresses causing the elastic deformation, to which the receiving member 64 and the plate 60 may be subjected, may also cause a slight amount of plastic deformation, but such slight amount of plastic deformation does not diminish the function of the receiving member 64 or the plate 60. However, as defined herein, the receiving member 64 and the plate 60 do not undergo substantial plastic deformation.

The receiving member 64 and the plate hole 62 may be configured to provide installation at room temperature by sizing the receiving member 64 to an appropriate size in relation to the plate hole 62 such that when a sufficient force is applied to the receiving member 64, the receiving member and a portion of the plate 60 elastically deform. Once the receiving member 64 is inserted into said plate hole 62, the force is released and the components each go back to their original size. Once installed, the receiving member 64 may be maintained in the plate hole 62 by the retaining lip 78. It is important to note that the installation forces placed on the receiving member 64 and the plate 60 that cause elastic deformation are larger than the forces placed on said receiving member 64 after installation of the complete device on the cervical spine. Therefore, the receiving member 64 may be maintained in the plate hole 62 by the retaining lip 78 without being forced out of the plate 60 by the naturally occurring forces found in the cervical spine.

In addition to the above, another method of installing the receiving member 64 within the plate holes 62 occurs during manufacturing by cooling the receiving member 64 to a temperature that effectively causes contraction of said receiving member 64. This causes the receiving member 64 to contract to a size that is small enough that the receiving member 64 may be slightly smaller than the plate hole 62 opening in order to effectuate the installation of said receiving member 64.

Insertion of the receiving member 64 into the plate hole 62 through cooling may include the following steps. First, inserting the receiving member 64 into liquid nitrogen, waiting a sufficient period of time for contraction of said receiving member 64 to begin, and removing the receiving member 64 from the liquid nitrogen after contraction of the receiving member 64 has occurred. Second, inserting the contracted receiving member 64 through the top of the plate hole 62 into an interior volume of said plate hole 62, and permitting the receiving member 64 to warm to room temperature thereby causing expansion of the receiving member 64 to its original shape and size. The period of time to accomplish the step of cooling the receiving member 64 to a sufficient temperature, to thereby cause the contraction of said receiving member 64, depends upon the properties of the material used to form the receiving member 64 and may be determined by one of ordinary skill in the art. Therefore, it will be appreciated that one of ordinary skill in the art, having possession of this disclosure, could determine the sufficient temperature and time to cause contraction of the receiving member 64 without undue experimentation.

It should be noted that any substance or method of cooling the receiving member 64 to a sufficient temperature to cause contraction, in addition to liquid nitrogen, may be used for contracting the receiving member 64. It should also be noted that the receiving member 64 may be manufactured from any suitable biocompatible material, including metal, such as titanium, stainless steel, cobalt-chromium-molybdenum alloy, titanium-aluminum vanadium alloy, or other suitable metallic alloys, or non-metallic biocompatible materials such as carbon-fiber, ceramic, bio-resorbable materials or if desired any suitable high strength plastic such as an ultra high molecular weight polyethylene. It should likewise be noted that the cooling of the receiving member 64 and subsequent placement into the plate holes 62 is only illustrative of one method of installation during the manufacturing process that may be implemented by the present invention and other methods of manufacture may also be used to accomplish the same or similar results.

After installation and subsequent warming, the receiving member 64 expands to its original shape and size, after which the retaining lip 78 maintains the receiving member 64 in the plate hole 62, thereby retaining the receiving member 64. The retaining lip 78 cooperates with a lower rim 80 to retain the receiving member 64 within the plate hole 62. The lower rim 80 extends laterally from the bottom surface 67 of the plate 60, precluding the receiving member 64 from advancing completely through the plate hole 62. Thus, the lower rim 80 provides a surface for the receiving member 64 to contact such that said receiving member 64 may be maintained within the plate hole 62 in conjunction with the retaining lip 78.

It should be noted that other embodiments of the retaining lip 78 are contemplated by the present invention, such as a depressable retaining lip 78 (seen best in FIG. 6). The depressable retaining lip 78 may be initially upright in an open position, referred to and illustrated in phantom-line as item 78A of FIG. 6, and has a pivot point 82 which permits the retaining lip 78 to be depressed downwardly with respect to the plate 60 into a lateral, closed position 78B. A process of installing a receiving member 64 includes inserting the receiving member 64 into the corresponding plate hole 62 with the retaining lip 78 in the open position 78A. After the receiving member 64 has been inserted into the plate hole 62, the retaining lip 78 may be depressed into the closed position 78B, thereby retaining the receiving member 64, which depressable retaining lip 78 functions similarly to the retaining lip 78 illustrated in FIG. 4.

It is important to note that the depressable retaining lip 78 of this embodiment and illustrated in FIG. 6 does not require the above described installation process of cooling the receiving member 64 to install said receiving member 64 into the plate hole 62 because of the depressability of the retaining lip 78, which can be opened and closed to permit the entrance of the receiving member 64. Additionally, the depressable retaining lip 78 permits the receiving member 64 to be either pre-installed during manufacturing, or by a surgeon or surgical staff member prior to or at the time of surgery.

In accordance with the features and combinations described above, a useful method of implanting the dynamic spinal bone fixation plate assembly onto a patient's spine includes the steps of:

(a) locating the spinal plate 60 on the patient's spine;

(b) inserting a driving tool 200 into the recess 94 formed in the head 96 of the fastener 70;

(c) inserting the shaft portion 92 of the fastener 70 through the receiving member 64 until the tip 98 engages the bone;

(d) securing the fastener 70 to the bone; and (e) advancing the fastener 70 until the tapered 72 section of the fastener 70 mates with the corresponding tapered sidewalls 68 of the receiving member 64, thus locking the fastener 70 to the plate 60.

It is to be understood that the present invention is applicable to any implant device or assembly for which the advantages of the invention can be used. For example, in addition to a spinal fixation apparatus, the invention may also be applied to serve in the form of a fastener-receiving member locking interface as part of the mechanics to lock an acetabular cup to a pelvis, or to lock a tibial tray to a tibial plate, or to lock stabilization plates to long bones, or as part of maxillo facial applications, or any suitable application.

Figure 9:
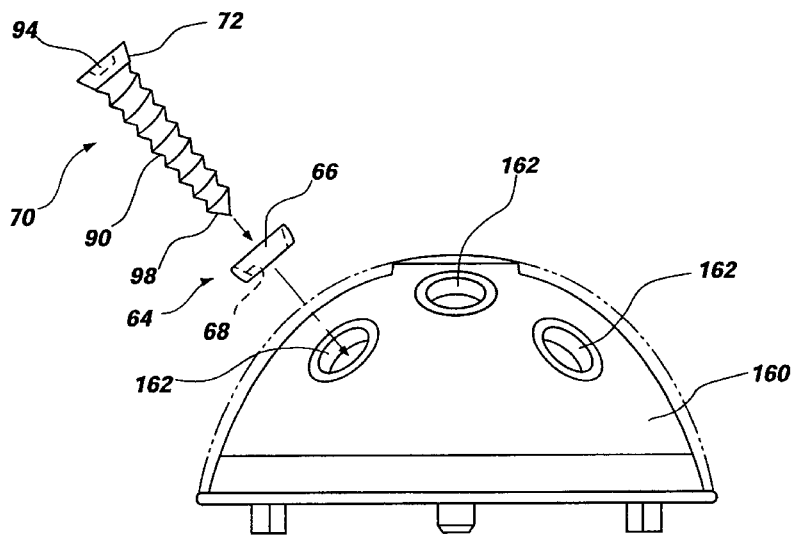
FIG. 9 is an exploded, side view of an alternative embodiment of the present invention illustrating a bone screw, a collet or receiving member, and an acetabular cup, made in accordance with the principles of the present invention.
Figure 10:
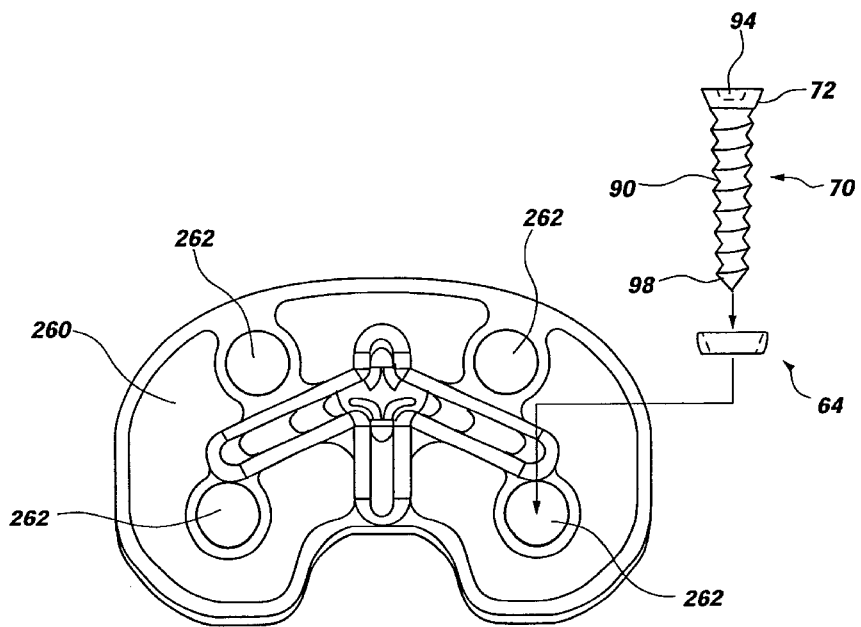
FIG. 10 is a top view of an alternative embodiment of the present invention illustrating a bone screw, a collet or receiving member, and a tibial implant, made in accordance with the principles of the present invention.

Turning now to FIGS. 9 and 10, wherein like reference numerals represent like structure in previous embodiments. FIG. 9 illustrates an alternative embodiment of the present invention as described in relation to the acetabular cup. FIG. 9 is an exploded view of a fastener 70, a receiving member 64 and an alternative embodiment of an attachment member illustrated as an acetabular cup 160. In the present embodiment, the acetabular cup 160 comprises at least one hole 162 configured for maintaining said receiving member 64 within the acetabular cup 160. The fastener 70, illustrated as a bone screw, may be configured for securing the acetabular cup 160 to the bone. The receiving member 64 and the fastener 70 may, therefore, be used with the acetabular cup 160 in accordance with the principles of the present invention, described more fully above.

FIG. 10 is an exploded view of another embodiment of the present invention. FIG. 10 specifically illustrates the fastener 70, the receiving member 64 and another alternative embodiment of the attachment member illustrated as a tibial tray 260. The tibial tray 260 comprises at least one tray hole 262 similar to the holes described in relation to the spinal plate 60 and the acetabular cup 160. Essentially, the structural features and principles described above in relation to the spinal plate 60 are also applicable to the tibial tray 260. Therefore, it should be noted that the features and principles of the present invention may be applied not only to the spinal plate 60, but also to the acetabular cup 160, the tibial tray 260 as well as other orthopedic devices not illustrated herein.

Those having ordinary skill in the relevant art will appreciate the advantages provided by the features of the present invention. It is a feature of the present invention to provide a spinal plate for stabilizing the human spine which is simple in design and manufacture. For example, the one-step self locking feature permits the surgeon to quickly and efficiently insert the fastener 70 into the spine without undue delay. Another feature of the present invention includes the fastener 70 and the receiving member 64 each having a tapered portion forming a quick and efficient self-locking taper connection. Yet another advantageous feature includes a constrained and semiconstrained plate 60 that may be achieved by the present invention for use with differing patient needs. Yet another feature of the present invention includes the advantage of using the fastener 70 and the receiving member 64 in several orthopedic situations to secure several different orthopedic devices to a bone, such as a vertebra, tibia, pelvis and other bones.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A spinal fixation apparatus for stabilizing a plurality of bone segments comprising:
   an elongate member having a first opening formed therethrough, said first opening being defined by a concave sidewall;
   a means for attaching the elongate member to at least one human vertebra of the spine, the means for attaching having a first portion and a second portion, the first portion having a tapered-exterior surface; and
   a receiving member configured for placement in said first opening and for receiving said means for attaching, said receiving member having a first aperture therethrough, said first aperture being defined by a tapered sidewall;
   wherein said tapered-exterior surface of the first portion of said means for attaching and the tapered sidewall of said receiving member matingly engage forming a locking friction fit between said means for attaching and said receiving member, and wherein said receiving member is configured and dimensioned relative to the first opening of the elongate member to remain movable within said first opening after implantation in a semiconstrained manner.

2. The spinal fixation apparatus for stabilizing a plurality of bone segments of claim 1, said elongate member further comprising a top surface, a bottom surface and a retaining member, said retaining member extending laterally from said first opening on said top surface of said elongate member for retaining said receiving member within said first opening.

3. The spinal fixation apparatus for stabilizing a plurality of bone segments of claim 1, said elongate member further comprising a depressable retaining lip, said depressable retaining lip having an upright, open position with respect to said elongate member and a pivot point such that said depressable retaining lip may pivotally rotate about said pivot point when said retaining lip depresses downwardly into a horizontal, closed position.

4. The spinal fixation apparatus for stabilizing a plurality of bone segments of claim 1, said elongate member further comprising a top surface, a bottom surface and a lower rim, said lower rim extending laterally from said first opening on said bottom surface to thereby support and maintain said receiving member within said first opening and preclude said receiving member from advancing completely through said first opening.

5. The spinal fixation apparatus for stabilizing a plurality of bone segments of claim 1, said second portion of said means for attaching having a male-external threading for threaded advancement into at least one of the plurality of bone segments.

6. The spinal fixation apparatus for stabilizing a plurality of bone segments of claim 1, said tapered exterior surface of the first portion forming a head of said means for attaching, said head having a top surface with a recess formed therein for receiving a driving instrument.

7. The spinal fixation apparatus for stabilizing a plurality of bone segments of claim 1, said means for attaching further comprising a blunt tip extending from said second portion.

8. The spinal fixation apparatus for stabilizing a plurality of bone segments of claim 1, wherein a portion of said receiving member comprises a larger diameter than a portion of said first opening.

9. The spinal fixation apparatus for stabilizing a plurality of bone segments of claim 1, said receiving member having a convex exterior surface for at least partially engaging said sidewall of said elongate member.

10. The spinal fixation apparatus for stabilizing a plurality of bone segments of claim 9, said convex exterior surface of said receiving member being smaller than said corresponding concave sidewall of said elongate member such that said receiving member may move relative to said first opening permitting micro-adjustments in said spinal fixation apparatus.

11. The spinal fixation apparatus for stabilizing a plurality of bone segments of claim 1, said elongate member having a second opening, said elongate member further having a longitudinal axis dividing a first side from a second side, said first and second openings being formed between a top and bottom surface of said elongate member, and the first opening being located in the first side and the second opening being formed in the second side.

12. The spinal fixation apparatus for stabilizing a plurality of bone segments of claim 11, wherein said first and second openings may be circularly shaped and have a circumferential edge defining a diameter of said first and second openings.

13. The spinal fixation apparatus for stabilizing a plurality of bone segments of claim 1, wherein said elongate member comprises a horizontal axis and said receiving member has a geometry such that said receiving member may be movable within said first opening of said elongate member without rotating 180 degrees within said first opening with respect to the horizontal axis.

14. A spinal fixation apparatus for stabilizing a plurality of bone segments comprising:
   an elongate member having a first opening formed therethrough, said first opening being defined by a concave sidewall;
   a means for attaching the elongate member to at least one human vertebra of the spine, the means for attaching having a first portion and a second portion, the first portion having a tapered-exterior surface; and a receiving member having a convex exterior surface configured and dimensioned for partially engaging the concave sidewall of said elongate member, said receiving member further having a first aperture formed therethrough, said first aperture being defined by a tapered sidewall;

wherein said tapered-exterior surface of the first portion of said means for attaching and the tapered sidewall of said receiving member matingly engage forming a locking friction fit between said means for attaching and said receiving member.

15. The spinal fixation apparatus for stabilizing a plurality of bone segments of claim 14, said elongate member further comprising a top surface, a bottom surface and a retaining member, said retaining member extending laterally from said first opening on said top surface of said elongate member for retaining said receiving member within said first opening.

16. The spinal fixation apparatus for stabilizing a plurality of bone segments of claim 14, said elongate member further comprising a depressable retaining lip, said depressable retaining lip having an upright, open position and a pivot point such that said depressable retaining lip may pivotally rotate about said pivot point when said retaining lip depresses downwardly into a horizontal, closed position.

17. The spinal fixation apparatus for stabilizing a plurality of bone segments of claim 14, said elongate member further comprising a top surface, a bottom surface and a lower rim, said lower rim extending laterally from said first opening on said bottom surface to thereby support and maintain said receiving member within said first opening and preclude said receiving member from advancing through said first opening.

18. The spinal fixation apparatus for stabilizing a plurality of bone segments of claim 14, said second portion of said means for attaching having a male-external threading for threaded advancement into at least one of said plurality of bone segments.

19. The spinal fixation apparatus for stabilizing a plurality of bone segments of claim 14, said tapered-exterior surface forming a head of said means for attaching, said head having a top surface with a recess formed therein.

20. The spinal fixation apparatus for stabilizing a plurality of bone segments of claim 14, said means for attaching further comprising a blunt tip extending from said second portion.

21. The spinal fixation apparatus for stabilizing a plurality of bone segments of claim 14, wherein a portion of said receiving member comprises a larger diameter than a portion of said first opening of said elongate member.

22. The spinal fixation apparatus for stabilizing a plurality of bone segments of claim 14, said convex exterior surface of said receiving member configured to be smaller than said corresponding concave sidewall of said elongate member such that said receiving member may move relative to said first opening causing micro-adjustments in said spinal fixation apparatus.

23. The spinal fixation apparatus for stabilizing a plurality of bone segments of claim 14, said elongate member having a second opening, said elongate member further having a longitudinal axis dividing a first side from a second side, said first and second opening being formed between a top and bottom surface of said elongate member, and the first opening being located in the first side and the second opening being formed in the second side.

24. The spinal fixation apparatus for stabilizing a plurality of bone segments of claim 23, wherein said first and second openings may be circularly shaped and each opening has a circumferential edge defining a diameter of said first and second openings.

25. The spinal fixation apparatus for stabilizing a plurality of bone segments of claim 14, wherein said elongate member comprises a horizontal axis and said receiving member has a geometry such that said receiving member may be movable within said first opening of said elongate member without rotating 180 degrees within said first opening with respect to the horizontal axis.

26. A spinal fixation apparatus for stabilizing a plurality of bone segments comprising:

an elongate member having a concave sidewall defining a first opening formed therethrough and a retaining portion extending from said first opening;

a means for attaching the elongate member to at least one human vertebra of the spine, the means for attaching having a first portion and a second portion, the first portion having a tapered-exterior surface; and a receiving member having a convex exterior surface configured and dimensioned for partially engaging the concave sidewall of said elongate member, said receiving member further having a tapered sidewall defining a first aperture therethrough;

wherein said tapered-exterior surface of the first portion of said means for attaching and the tapered sidewall of said receiving member being disposed in mating engagement forming a locking friction fit, and said receiving member being further configured and dimensioned such that said receiving member may be movable within the first opening even after the locking friction fit has been formed such that the retaining portion maintains said receiving member within said first opening.

27. The spinal fixation apparatus for stabilizing a plurality of bone segments of claim 26, said elongate member further comprising a top surface, a bottom surface and a lower rim, said retaining member extending laterally from said first opening on the top surface and said lower rim extending laterally from said first opening on said bottom surface to thereby support and maintain said receiving member within said first opening and preclude said receiving member from advancing through said first opening.

28. The spinal fixation apparatus for stabilizing a plurality of bone segments of claim 26, said second portion of said means for attaching having a male-external threading for threaded advancement into at least one of said plurality of bone segments.

29. The spinal fixation apparatus for stabilizing a plurality of bone segments of claim 26, said tapered exterior surface forming a head of said means for attaching, said head having a top surface with a recess formed therein.

30. The spinal fixation apparatus for stabilizing a plurality of bone segments of claim 26, said means for attaching further comprising a blunt tip extending from said second portion.

31. The spinal fixation apparatus for stabilizing a plurality of bone segments of claim 26, wherein a portion of said receiving member comprises a larger diameter than a portion of said first opening of said elongate member.

32. The spinal fixation apparatus for stabilizing a plurality of bone segments of claim 26, said elongate member having a second opening, said elongate member further having a longitudinal axis dividing a first side from a second side, said first and second opening being formed between a top and bottom surface of said elongate member, and the first opening being located in the first side and the second opening being formed in the second side.

33. The spinal fixation apparatus for stabilizing a plurality of bone segments of claim 32, wherein said first and second openings may be circularly shaped and have a circumferential edge defining a diameter of said first and second openings.

34. The spinal fixation apparatus for stabilizing a plurality of bone segments of claim 26, wherein said elongate member comprises a horizontal axis and said receiving member has a geometry such that said receiving member may be movable within said first opening of said elongate member without rotating 180 degrees within said first opening with respect to the horizontal axis.

35. A spinal fixation apparatus for stabilizing a plurality of bone segments comprising:
   an elongate member comprising a first portion and a second portion, said elongate member having a first opening, said first opening being defined by a sidewall;
   a depressable retaining portion formed in the first portion of said elongate member and interconnected with said sidewall of said first opening, the depressable retaining portion having a substantially upright, open position and substantially horizontal, closed position with respect to said elongate member; and
   a receiving member configured for receiving a fastener and having an exterior surface for engaging the sidewall of said first opening;
   wherein the depressable retaining portion may be initially in the upright, open position allowing the passage of the receiving member into the first opening, thereafter the depressable retaining portion may be depressed, closing said depressable retaining portion and maintaining the receiving member within said first opening.

36. The spinal fixation apparatus for stabilizing a plurality of bone segments of claim 35, said first portion and said second portion of said elongate member being a top surface and a bottom surface respectively.

37. The spinal fixation apparatus for stabilizing a plurality of bone segments of claim 35, said elongate member further comprising a lower rim, said lower rim extending laterally from said first opening on said second portion of said elongate member to thereby support and maintain said receiving member within said first opening and preclude said receiving member from advancing completely through said first opening.

38. The spinal fixation apparatus for stabilizing a plurality of bone segments of claim 35, wherein said fastener further comprises a means for attaching said apparatus to the plurality of bone segments, said means for attaching having a tapered-head portion and a male-external threaded portion for threaded advancement into at least one of the plurality of bone segments.

39. The spinal fixation apparatus for stabilizing a plurality of bone segments of claim 38, said tapered-head portion having a top surface with a recess formed therein for receiving a driving instrument.

40. The spinal fixation apparatus for stabilizing a plurality of bone segments of claim 38, said means for attaching further comprising a blunt tip extending from said male-external threaded portion.

41. The spinal fixation apparatus for stabilizing a plurality of bone segments of claim 35, said receiving member having a larger diameter than said first opening when said retaining portion is in the horizontal, closed position.

42. The spinal fixation apparatus for stabilizing a plurality of bone segments of claim 35, said exterior surface of said receiving member being a convex shaped exterior surface for partially engaging said sidewall of said elongate member.

43. The spinal fixation apparatus for stabilizing a plurality of bone segments of claim 42, wherein said sidewall of said elongate member having a concave shape, wherein said convex exterior surface of said receiving member being smaller than said corresponding concave sidewall of said elongate member such that said receiving member may move relative to said first opening permitting microadjustments in said spinal fixation apparatus.

44. The spinal fixation apparatus for stabilizing a plurality of bone segments of claim 35, said receiving member having a first aperture, said first aperture being defined by a tapered sidewall, said fastener further comprising a means for attaching said apparatus to the plurality of bone segments, said means for attaching having a tapered first portion and a second portion, wherein said second portion may be inserted through said first aperture engaging said tapered first portion with said tapered sidewall forming a locking friction fit between said means for attaching and said receiving member.

45. The spinal fixation apparatus for stabilizing a plurality of bone segments of claim 35, said elongate member having a second opening, said elongate member further having a longitudinal axis dividing a first side from a second side, said first and second opening being formed between a top and bottom surface of said elongate member, and the first opening being located in the first side and the second opening being formed in the second side.

46. The spinal fixation apparatus f or stabilizing a plurality of bone segments of claim 45, wherein said first and second openings may be circularly shaped and have a circumferential edge defining a diameter of said first and second openings.

47. The spinal fixation apparatus for stabilizing a plurality of bone segments of claim 35, wherein said elongate member comprises a horizontal axis and said receiving member has a geometry such that said receiving member may be movable within said first opening of said elongate member without rotating 180 degrees within said first opening with respect to the horizontal axis.

48. A spinal fixation apparatus for stabilizing a plurality of bone segments comprising:
   an elongate member comprising a top portion and a bottom portion, said elongate member having a first opening formed therethrough, said first opening being defined by a concave sidewall;
   a means for attaching the elongate member to at least one human vertebra of the spine, the means for attaching having a first portion and a second portion, the first portion having a tapered-exterior surface, and the second portion having external threads thereon for insertion into at least one of the plurality of bone segments; and
   a receiving member having a convex exterior surface for engaging the concave sidewall of said elongate member, said receiving member further having a first aperture formed therethrough for receiving said means for attaching, said first aperture being defined by a tapered sidewall;
   wherein the second portion of the means for attaching may be inserted through the first aperture of the receiving member and into at least one of the plurality of bone segments; and
   wherein the tapered-exterior surface of the first portion of said means for attaching and the tapered sidewall of said receiving member may be matingly engaged in a friction fit, and wherein said receiving member is configured and dimensioned relative to the first opening of the elongate member to remain movable within said first opening after implantation in a semiconstrained manner.

49. The spinal fixation apparatus for stabilizing a plurality of bone segments of claim 48, said elongate member further comprising a retaining member, said retaining member extending laterally from said first opening on said top surface for retaining said receiving member within said first opening.

50. The spinal fixation apparatus for stabilizing a plurality of bone segments of claim 48, said elongate member further comprising a depressable retaining lip, said depressable retaining lip having an upright, open position with respect to said elongate member and a pivot point such that said depressable retaining lip may pivotally rotate about said pivot point when said retaining lip depresses downwardly into a horizontal, closed position.

51. The spinal fixation apparatus for stabilizing a plurality of bone segments of claim 48, said elongate member further comprising a lower rim, said lower rim extending laterally from said first opening on said bottom surface to thereby support and maintain said receiving member within said first opening and preclude said receiving member from advancing completely through said first opening.

52. The spinal fixation apparatus for stabilizing a plurality of bone segments of claim 48, said tapered exterior surface forming a head of said means for attaching, said head having a top surface with a recess formed therein for receiving a driving instrument.

53. The spinal fixation apparatus for stabilizing a plurality of bone segments of claim 48, said means for attaching further comprising a blunt tip extending from said second portion.

54. The spinal fixation apparatus for stabilizing a plurality of bone segments of claim 48, wherein a portion of said receiving member comprises a larger diameter than a portion of said first opening.

55. The spinal fixation apparatus for stabilizing a plurality of bone segments of claim 48, wherein said convex exterior surface partially engages said concave sidewall of said elongate member.

56. The spinal fixation apparatus for stabilizing a plurality of bone segments of claim 48, said convex exterior surface of said receiving member being smaller than said corresponding concave sidewall of said elongate member such that said receiving member may move relative to said first opening permitting micro-adjustments in said spinal fixation apparatus.

57. The spinal fixation apparatus for stabilizing a plurality of bone segments of claim 48, said elongate member having a second opening, said elongate member further having a longitudinal axis dividing a first side from a second side, said first and second opening being formed between a top and bottom surface of said elongate member, and the first opening being located in the first side and the second opening being formed in the second side.

58. The spinal fixation apparatus for stabilizing a plurality of bone segments of claim 57, wherein said first and second openings may be circularly shaped and have a circumferential edge defining a diameter of said first and second openings.

59. The spinal fixation apparatus for stabilizing a plurality of bone segments of claim 48, wherein said elongate member comprises a horizontal axis and said receiving member has a geometry such that said receiving member may be movable within first opening of said elongate member without rotating 180 degrees within said first opening with respect to the horizontal axis.

60. A method of assembling a spinal fixation apparatus comprising the steps of:
   obtaining an elongate member comprising a first portion and a second portion, the elongate member further having a first opening with a predetermined dimension;
   obtaining a receiving member configured and dimensioned to have an outside diameter larger than said first opening with said predetermined dimension;
   cooling the receiving member to a temperature sufficient for causing the receiving member to contract such that the receiving member may be inserted into said first opening with said predetermined dimension in said elongate member;
   heating the receiving member to thereby cause said receiving member to expand back to said receiving member's original size and shape.

61. The method of assembling a spinal fixation apparatus of claim 60, wherein the step of cooling the receiving member further includes inserting said receiving member into liquid nitrogen to thereby cause contraction of said receiving member.

62. The method of assembling a spinal fixation apparatus of claim 60, wherein obtaining said elongate member further includes the step of providing said elongate member with a retaining member, said retaining member extending laterally from said first opening on said first portion of said elongate member for retaining said receiving member within said first opening.

63. The method of assembling a spinal fixation apparatus of claim 60, wherein obtaining said elongate member further includes the step of providing said elongate member with a depressable retaining lip, said depressable retaining lip having an upright, open position with respect to said elongate member and a pivot point such that said depressable retaining lip may pivotally rotate about said pivot point when said retaining lip depresses downwardly into a horizontal, closed position.

64. The method of assembling a spinal fixation apparatus of claim 60, wherein obtaining said elongate member further includes the step of providing said elongate member with a lower rim, said lower rim extending laterally from said first opening on second portion to thereby support and maintain said receiving member within said first opening and preclude said receiving member from advancing completely through said first opening.

65. The method of assembling a spinal fixation apparatus of claim 60, wherein the method further comprises the step of attaching said spinal fixation apparatus to at least one vertebra.

66. The method of assembling a spinal fixation apparatus of claim 60, wherein attaching said spinal fixation apparatus includes using a bone screw having a tapered head portion and a threaded shank portion for advancing said bone screw into a bone, said tapered head portion having a top surface with a recess formed therein for receiving a driving instrument.

67. The method of assembling a spinal fixation apparatus of claim 66, wherein obtaining said receiving member further includes the step of providing said receiving member with a first aperture formed therethrough, said first aperture being defined by a tapered sidewall for mating engagement with said tapered head portion forming a locking friction fit.

68. The method of assembling a spinal fixation apparatus of claim 60, wherein obtaining said receiving member further includes the step of providing said receiving member with a larger diameter than said first opening.

69. The method of assembling a spinal fixation apparatus of claim 60, wherein obtaining said elongate member further includes the step of providing said first opening with a concave sidewall defining said first opening.

70. The method of assembling a spinal fixation apparatus of claim 69, wherein obtaining said receiving member further includes the step of providing said receiving member with a convex exterior surface for partially engaging said concave sidewall of said elongate member.

71. The method of assembling a spinal fixation apparatus of claim 70, wherein obtaining said receiving member further includes the step of providing said receiving member with said convex surface being smaller than said corresponding concave sidewall of said elongate member and thereby providing movement of said receiving member within said first opening permitting micro-adjustments in said spinal fixation apparatus.

72. The method of assembling a spinal fixation apparatus of claim 60, wherein obtaining said elongate member further includes the step of providing said elongate member with a second opening, said elongate member further having a longitudinal axis dividing a first side from a second side, said first and second opening being formed between said first and second portions of said elongate member, and the first opening being located in the first side and the second opening being formed in the second side, wherein said first and second openings may be circularly shaped and have a circumferential edge defining a diameter of said first and second openings.

73. The method of assembling a spinal fixation apparatus of claim 60, wherein obtaining said elongate member further includes the step of providing said elongate member with a horizontal axis and obtaining said receiving member further includes the step of providing said receiving member with a geometry such that said receiving member may be movable within said first opening of said elongate member without rotating 180 degrees within said first opening with respect to the horizontal axis.

74. A method of attaching a spinal fixation device to the spinal region comprising the steps of:

locating an elongate member comprising a first portion and a second portion, said elongate member having a concave sidewall defining a first opening formed therethrough;

obtaining a receiving member having a convex exterior surface for engaging the concave sidewall of said elongate member, said receiving member further having a tapered sidewall defining a first aperture therethrough;

inserting a fastener having an upper portion and a lower portion, the upper portion having a tapered-exterior surface, and the lower portion having external threads thereon for insertion through said first aperture of said receiving member and into a vertebral bone;

intercoupling the tapered-exterior surface of the fastener with the tapered sidewall of the receiving member through continual insertion of the lower portion of fastener into the vertebral bone until said tapered-exterior surface engages said tapered sidewall in a locking friction fit, and wherein said receiving member is configured and dimensioned relative to the first opening of the elongate member to remain movable within said first opening after implantation in a semi-constrained manner.

75. A method of attaching a spinal fixation device to the spinal region comprising the steps of:

locating an elongate member having a sidewall defining a first opening formed therethrough onto the spinal region; adjusting a position of a previously installed receiving member, having an exterior surface, within the first opening such that the exterior surface partially engages the sidewall of the elongate member such that said receiving member may be rotated within said first opening of said elongate member, said receiving member further having a tapered sidewall defining a first aperture therethrough; and inserting a fastener through the first aperture of said receiving member, the fastener having an upper portion and a lower portion, the upper portion having a tapered-exterior surface, and the lower portion having external threads thereon for insertion into a vertebral bone;

wherein placing the lower portion of said fastener through said first aperture in said receiving member and screwing said lower portion into the vertebral bone of the spine causes the tapered-exterior surface to matingly engage the tapered sidewall of said receiving member such that an friction locking fit occurs.

76. A method of attaching a spinal fixation device to the spinal region comprising the steps of:

locating an elongate support member having a sidewall defining a first opening formed therethrough onto the spinal region, the elongate support member further having a depressable retaining lip with a substantially upright, open position and a substantially horizontal, closed position;

positioning a receiving member within the first opening of the elongate support member while the depressable retaining lip resides in the upright, open position, the receiving member having an exterior surface for partially engaging the sidewall of the elongate member such that said receiving member may be rotated within said first opening of said elongate member, said receiving member further having a tapered sidewall defining a first aperture therethrough;

depressing the depressable retaining lip thereby closing said depressable retaining lip;

inserting a fastener through the first aperture of the receiving member, the fastener having a first portion and a second portion, the first portion having a tapered-exterior surface for matingly engaging the tapered sidewall of the first aperture, the second portion having external threads thereon for insertion into the vertebral bone;

wherein placing the second portion of said fastener through said first aperture in said receiving member and screwing said second portion into the vertebral bone of the spine causes the tapered-exterior surface to matingly engage the tapered sidewall of said receiving member such that an friction locking fit occurs.

77. A fixation apparatus for stabilizing a plurality of bone segments comprising:

an attachment member having a first opening formed therethrough, said first opening being defined by a concave sidewall;

a fastener for attaching the attachment member to at least one human bone segment, the fastener having a first portion and a second portion, the first portion having a tapered-exterior surface; and a receiving member configured for placement in said first opening and for receiving said fastener therein and wherein said receiving member is configured and dimensioned relative to the first opening of the attachment member to remain movable within said first opening after implantation in a semiconstrained manner, said receiving member having a first aperture therethrough, said first aperture being defined by a tapered sidewall;

wherein said tapered-exterior surface of the first portion of said fastener and the tapered sidewall of said receiving member matingly engage forming a locking friction fit between said fastener and said receiving member.

78. A spinal fixation apparatus for stabilizing a plurality of bone segments comprising:

an elongate member having a first opening formed therethrough, said first opening being defined by a concave sidewall;

a fastener for attaching the elongate member to at least one human vertebra of the spine, the fastener having a first portion and a second portion, the first portion having a tapered-exterior surface; and a receiving member having a convex exterior surface configured and dimensioned for partially engaging the concave sidewall of said elongate member, said receiving member further having a first aperture formed therethrough, said first aperture being defined by a tapered sidewall;

wherein said tapered-exterior surface of the first portion of said fastener and the tapered sidewall of said receiving member matingly engage forming a locking friction fit between said fastener and said receiving member.

79. A fixation apparatus for stabilizing a plurality of bone segments comprising:

an attachment member having a first opening formed therethrough, said first opening being defined by a concave sidewall;

a fastener for attaching the attachment member to at least one human bone segment, the fastener having a first portion and a second portion, the first portion having a tapered-exterior surface; and a non-expandable receiving member configured for placement in said first opening and wherein said receiving member is configured and dimensioned relative to the first opening of the attachment member to remain movable within said first opening after implantation in a semiconstrained manner, said receiving member having a first aperture therethrough for receiving said fastener therein, said first aperture being defined by a tapered sidewall;

wherein said tapered-exterior surface of the first portion of said fastener and the tapered sidewall of said receiving member matingly engage without expanding said receiving member forming a locking friction fit between said fastener and said receiving member.

80. A fixation apparatus for stabilizing a plurality of bone segments comprising:

an attachment member having a first opening formed therethrough, said first opening being defined by a concave sidewall having a first radius of curvature;

a fastener for attaching the attachment member to at least one human bone segment, the fastener having a first portion and a second portion, the first portion having a tapered-exterior surface; and a receiving member having a first aperture formed therethrough for receiving said fastener therein, said first aperture being defined by a tapered sidewall, said receiving member being configured for placement in said first opening and having an exterior surface that comprises a second radius of curvature that is different than said first radius of curvature of the first opening of said attachment member;

wherein the difference in radii of curvature between said first radius of curvature and said second radius of curvature creates a zone of contact between the concave sidewall of the first opening and the exterior surface of the receiving member thereby locking said receiving member to said attachment member; and wherein said tapered-exterior surface of the first portion of said fastener and the tapered sidewall of said receiving member matingly engage without expanding said receiving member to thereby form a locking friction fit between said fastener and said receiving member.

81. A fixation apparatus for stabilizing a plurality of bone segments comprising:

an attachment member having a first opening formed therethrough;

a fastener for attaching the attachment member to at least one human bone segment, the fastener having a first portion and a second portion, the first portion having a tapered-exterior surface; and a receiving member having a first aperture formed therethrough for receiving said fastener therein, said first aperture being defined by a tapered sidewall, said receiving member being configured for placement in said first opening; and wherein said tapered-exterior surface of the first portion of said fastener and the tapered sidewall of said receiving member are configured and dimensioned to matingly engage together without causing expansion of said receiving member to thereby form a locking friction fit between said fastener and said receiving member.

82. The spinal fixation apparatus for stabilizing a plurality of bone segments of claim 81, wherein said receiving member is configured and dimensioned relative to the first opening of the attachment member to remain movable within said first opening after implantation in a semiconstrained manner, and wherein the attachment member comprises an elongate cervical plate configured and dimensioned f or attachment to the cervical spine.

83. A spinal fixation apparatus for stabilizing a plurality of bone segments comprising:

an elongate spinal plate comprising a top surface and a bottom surface, and a first side and a second side, said elongate spinal plate having a longitudinal axis dividing the first side from the second side, said elongate spinal plate further having a horizontal axis and at least one pair of concave sidewalls defining at least one pair of openings formed between the top and bottom surface and the at least one pair of openings being located in each of the first side and second side, said at least one pair of openings being circularly shaped and having a circumferential edge further defining a diameter of said at least one pair of openings, and at least one elongate hole extending between the top surface and the bottom surface, being formed along the longitudinal axis of said elongate spinal plate and located between said first and second side;

a retaining lip extending inward from said at least one pair of openings, forming a portion of the circumferential edge of said elongate spinal plate and being integrally formed in the top surface of said elongate spinal plate;

a lower rim extending inward from said at least one pair of openings, being integrally formed in the bottom surface of said elongate spinal plate, such that the at least one pair of concave sidewalls may be located between the retaining lip and the lower rim;

a fastener for attaching the elongate spinal plate to at least one human vertebra of the spine, comprising a head portion and a shank portion, the head portion having a tapered-exterior surface and a recess formed in said head portion for receiving a screw driving instrument, the shank portion having an external threading thereon for advancing said fastener into at least one of the plurality of bone segments of the spine; and a receiving member having a convex exterior surface for partially engaging the at least one pair of concave sidewalls of said elongate spinal plate, the receiving member further having a tapered sidewall defining a first aperture therethrough for receiving said head portion of said fastener, said convex exterior surface having a diameter larger than the diameter of each of said at least one pair of openings such that the receiving member may be maintained within each of said at least one pair of openings without fully engaging said at least one pair of concave sidewalls to thereby permit adjusting of said receiving member within said at least one pair of openings during the settling of said elongate spinal plate, wherein said receiving member has a geometry such that said receiving member may be movable within said at least one pair of openings of said elongate spinal plate without rotating 180 degrees within said at least one pair of openings with respect to the horizontal axis of the elongate spinal plate;

wherein the shank portion of the fastener may be inserted through the first aperture of the receiving member and into at least one of the plurality of bone segments, and causing a mating engagement between the tapered-exterior surface of the head portion of said fastener and the tapered sidewall of said receiving member forming a locking friction fit, such that said receiving member may be movable within said at least one pair of openings with respect to said elongate spinal plate.

* * * * *